United States Patent [19]

Bauer, Jr. et al.

[11] Patent Number: 5,789,613

[45] Date of Patent: Aug. 4, 1998

[54] REDUCTION OF CARBONYL IMPURITIES IN α, β-UNSATURATED ACIDS AND ESTERS

[75] Inventors: William Bauer, Jr., Huntingdon Valley; Nelson Ivan Quiros, Telford, both of Pa.

[73] Assignee: Rohm and Haas Company, Philadelphia, Pa.

[21] Appl. No.: 848,002

[22] Filed: Apr. 28, 1997

Related U.S. Application Data

[60] Provisional application No. 60/016,989, May 7, 1996.

[51] Int. Cl.$^6$ .................................................. C07C 67/48
[52] U.S. Cl. .................................................. 560/218
[58] Field of Search ............................................. 560/218

[56] References Cited

U.S. PATENT DOCUMENTS

| 4,187,382 | 2/1980 | Cowherd et al. |         |
|-----------|--------|-----------------|---------|
| 5,488,141 | 1/1996 | Bauer, Jr. et al. | 560/218 |

FOREIGN PATENT DOCUMENTS

| 29 13 218 | 4/1979 | Germany . |
| 8183633 | 10/1983 | Japan . |

OTHER PUBLICATIONS

"Kinetics of the One–Electron Transfer Reaction of Trimethyl Phosphite with Quinones", J. Org. Chem. vol. 38, No. 19, 1973.

"Oxyphosphoranes", Chem. Res., vol. 1, pp. 168–174, 1968.

"Charge Transfer Reactions of Trivalent Phosphorus Compounds with P–Quinones" Phosphorus and Sulphur, Gordon and Breach Science Publishers, Ltd., Great Britain, vol. 5, pp. 61–66, 1978.

"Organic Compounds with Pentavalent Phosphorus." Fausto Ramirez, N. B. Desai, J. Amer. Chem. Soc., vol. 85, pp. 3252–3258, 1963.

*Primary Examiner*—Paul J. Killos
*Attorney, Agent, or Firm*—John Lemanowicz; Kevin Gironda

[57] ABSTRACT

The invention provides a process for reducing one or more carbonyl impurity present in a monomer of an α,β-unsaturated carboxylic acid or its alkyl ester by treating the monomer containing the carbonyl impurities with a trialkyl phosphite or a triaryl phosphite.

11 Claims, No Drawings

REDUCTION OF CARBONYL IMPURITIES IN α, β-UNSATURATED ACIDS AND ESTERS

This invention relates to a method of reducing carbonyl impurities present in a monomer of an α,β-unsaturated carboxylic acid or its alkyl ester, preferably in acrylic acid or methacrylic acid (hereinafter "(meth)acrylic acid") or acrylic alkyl ester or methacrylic alkyl ester (hereinafter "(meth)acrylic alkyl ester").

Processes for producing monomers of α,β-unsaturated carboxylic acids or their esters, such as those of the (meth) acrylic acids and alkyl esters, often incorporate oxidative steps, such as in the vapor phase oxidation of propylene, isobutylene, tertiary butanol, methacrolein, acrolein, or isobutyraldehyde to afford the unsaturated acid followed by esterification to the ester. These monomer processes often are treated with polymerization inhibitors such as benzoquinones or hydroquinones, which easily undergo oxidation to the corresponding benzoquinones. In addition, certain (meth)acrylic esters may contain 2,3 butanedione (also termed "diacetyl") and other diones as impurities. These quinones and diones are undesirable carbonyl impurities in a final α,β-unsaturated carboxylic acid or its alkyl ester product monomer because they add color to the monomer, or they may interact with other reactants which are intended to react with the product monomer in subsequent reactions, or they may add color to a polymer product polymerized from the monomer, or react to form additional colored impurities, or they may directly inhibit other subsequent reactions of the final product monomer. Additionally, these quinones and diones may interfere with subsequent purification of the monomer and also may react with inhibitors present to prevent premature free radical polymerization of the monomer. For these reasons, quinones and/or diones are undesirable impurities and their levels must be reduced for some uses of the monomer. Their reduction is particularly important for the (meth)acrylic monomers which are widely used in producing polymers having optical clarity and low color and haze.

Para-benzoquinones are known to react with trialkyl phosphites. For example, Ramirez and Desai (*J. of Am. Chem. Soc.*, 85, 1963) reported that chloranil and related benzoquinones react with trimethyl phosphite to afford the methyl ethers of the hydroquinone monophosphates, and reported an analogous reaction with a-dicarbonyl compounds such as o-benzoquinones and 2,3-butanedione. Triphenyl phosphite has been used to thermally pretreat a diol before reacting the diol with (meth)acrylic acid (U.S. Pat. No. 4,187,382). The diol pretreatment reduced the tendency of the reaction mixture to polymerize, consequently reducing the level of conventional phenolic polymerization inhibitor required. Similar polymerization inhibition improvement was obtained by using phosphite esters, typically in combination with phenols, during esterification of (meth)acrylic acid (DE Application No. 29 13 218), however a combination of the reagents was required for effective inhibition. Further, distillation alone of a carbonyl-containing monomer usually is ineffective in removing some impurities, particularly diacetyl, because the impurity may codistill with the monomer.

A continuing problem in the art of producing α,β-unsaturated carboxylic acids or their esters, particularly (meth)acrylic acid or ester monomers, is that there is no simple, effective treatment useful in reducing the level of quinones and diones in the respective acids and esters after they have been prepared. Distillation alone is generally not effective because carbonyl impurities are carried over into the distillate. From an operational standpoint it is more convenient, effective and desirable to reduce undesirable carbonyl impurities in a monomer without incurring the cost of an additional pretreatment step or using additional reagents in combination.

The current invention provides a process for reducing carbonyl impurity in a single treatment after the monomer has been produced. We have discovered that certain phosphite esters exhibit remarkable selectivity in their reaction with one or more carbonyl impurities typically present in a reaction mixture obtained in the production of a monomer of α,β-unsaturated carboxylic acid or its alkyl ester, particularly of (meth)acrylic acid or (meth)acrylic alkyl ester. Thus, there is provided a process for reducing carbonyl impurity present in an α,β-unsaturated carboxylic acid or its alkyl ester, comprising (a) admixing (i) a monomer selected from the group consisting of an α,β-unsaturated carboxylic acid, an α,β-unsaturated carboxylic acid alkyl ester, and mixtures thereof, the monomer containing a carbonyl impurity present at an original level of at least 50 parts per million, with (ii) a phosphite ester selected from the group consisting of a trialkyl phosphite and a triphenyl phosphite, wherein the molar ratio of phosphite ester to carbonyl impurity in the monomer is 1:1 to 50:1, thereby forming a treated monomer mixture; and b) holding the treated monomer mixture at a temperature of from 20° C. to 150° C., thereby reducing the carbonyl impurity in the monomer by at least 10 weight percent of the original level of the carbonyl impurity.

Further, there is provided a purified monomer comprising (a) a monomer selected from the group consisting of an α,β-unsaturated carboxylic acid, an α,β-unsaturated carboxylic acid alkyl ester, and mixtures thereof, the monomer containing a carbonyl impurity present at an original level of at least 50 parts per million; and b) a phosphite ester selected from the group consisting of trialkyl phosphite and triphenyl phosphite, wherein the phosphite ester is present in a molar ratio of from 1:1 to 50:1 of the original level of the carbonyl impurity in the monomer.

The purified monomer resulting from the process just described, by having its original carbonyl impurity reduced by at least 10 percent, advantageously has: 1) less color than untreated monomer; 2) polymeric products produced from the purified monomer having lower light transmission loss characteristics; and 3) less tendency to polymerize, thus increasing the safety in shipping and handling of the purified monomer.

DETAILED DESCRIPTION OF THE INVENTION

Carbonyl impurity-containing monomers which are purified using the inventive process include α,β-unsaturated carboxylic acids having from 3 to 10 carbon atoms, such as acrylic, methacrylic, 2-butenoic, cyclohexenoic, maleic, and itaconic acid, and the corresponding alkyl esters of these acids. The esters typically are obtained from an alkyl alcohol having an alkyl group of from 1 to 10 carbon atoms (conventionally described as a "$C_1$–$C_{10}$ alkyl group") such as from methanol, ethanol, normal and iso-propanol, the primary, secondary, iso- and tertiary butanols, cyclohexanol, octanol, 2-ethyl hexanol, $C_1$–$C_{10}$ glycols, decanol, and their isomers. Preferred acids are the $C_3$–$C_5$ α,β-unsaturated carboxylic acids and their corresponding alkyl esters obtained from $C_1$–$C_5$ alkyl alcohols; more preferred are acrylic and methacrylic acid and their corresponding $C_1$–$C_5$ alkyl esters; most preferred are acrylic acid, methacrylic acid, ethyl acrylate, butyl acrylate, and methyl methacrylate because of their commercial importance.

A molar ratio of up to 50:1 of a trialkyl phosphite, or a triaryl phosphite, or a mixture of these, relative to the sum of the moles of one or more carbonyl impurity originally present in the monomer, effectively reacts with, and substantially reduces, the carbonyl impurity in the monomer. The selective reaction occurs under mild thermal conditions, that is from about ambient (i.e., 20°–25° C.) to 150° C., even though it is carried out in the presence of a vast excess of the α,β-unsaturated acid or ester monomer relative to the impurity. The selective reaction is believed to generate from the impurity a high boiling, "heavy" adduct which remains in the treated monomer mixture or, alternatively, may be separated from the monomer via known physical methods such as distillation. The selective reaction of this new process, carried out in the impurity-containing monomer, generates an α,β-unsaturated carboxylic acid or alkyl ester as a purified monomer having substantially reduced carbonyl impurity. The reduced impurity level generally affords measurably lower color in the purified monomer (and its polymer) and enhanced stability of the monomer to free radical polymerization.

The invention is particularly useful when a polymerization inhibitor system utilized in the manufacture or storage of the monomeric α,β-unsaturated carboxylic acid or its ester (henceforth abbreviated simply as "acid or ester monomer") contains p-benzoquinone or 1,4-hydroquinone, or when the acid or ester monomer is to be used for applications where light transmittance losses or reductions through a resulting polymer product need to be minimized, such as in uses for optical applications. Examples of purified monomer applications include monomer use in preparing polymers from which articles may be produced in a form such as an optical fiber, an architectural or an automotive light transmission fiber or "pipe," such as in rigid or flexible light pipe of diameter up to 15 millimeters, and other polymers requiring low yellow color and efficient light transmittance such as in light diffusers or light reflectors. The polymers prepared from the purified monomer of the invention are produced by polymerization methods known in the art, such as by free-radical or condensation polymerization.

The original carbonyl impurity level in the acid or ester monomer before treatment typically is at least 50 parts per million (ppm) and may be as high as 600 ppm in quinone or hydroquinone, and 500 ppm in diacetyl impurity; higher levels could be present. The impurity-containing monomers typically are distinctly yellow in color, typically estimated to be at least 100 on the platinum-cobalt (or the identical APHA) color scale, and often are estimated above 200 color. After treatment by the process of the invention, however, quinone and diacetyl levels are reduced to substantially lower levels, meaning an impurity reduction of at least 10 weight percent, preferably of at least 50%, and more preferably of at least 80%, of the original level in the carbonyl impurity-containing monomer. The color of the monomer, and of the polymer produced from the monomer, generally improves (i.e. is reduced) in approximate proportion to the extent of reduction in the concentration of these carbonyl impurities; thus, purified monomers of the invention generally will have platinum-cobalt scale colors below 100, preferably below 80, and more preferably below 50.

The phosphite esters of the invention which have been found effective include the trialkyl phosphites and the triaryl phosphites, or a mixture of these. The phosphite ester alkyl may be from $C_1$ to $C_{12}$ alkyl, and lower alkyl groups such as those having from 1 to 4 carbon atoms are preferred. The phosphite aryl may be phenyl or substituted phenyl groups, such as, for example, anisyl, hydroxy-phenyl, and amino-phenyl. Phosphite esters such as trimethyl phosphite, triethyl phosphite, tributyl phosphite and triphenyl phosphite are preferred phosphite esters because of their relatively low cost and commercial availability.

The holding time required to substantially reduce carbonyl levels will vary with temperature, concentration of the phosphite ester and the impurity, and the degree of impurity reduction desired. The holding temperature typically should remain below the boiling point of any solvent used or below the 1-atmosphere pressure boiling point of the monomer acid or ester treated to minimize polymerization of the monomer. As previously mentioned, temperatures from ambient up to a maximum of 150° C. are used, but preferred ranges are from 60° to 100° C., and more preferred are 80° to 90° C., because accelerated reaction rates are achieved over the rate at ambient temperature, without inducing premature monomer polymerization which may occur at temperatures above about 100° C. Holding times of only one to several minutes may be effective in these preferred ranges, and may be up to one or more days at ambient temperature.

The carbonyl impurity-containing acid or ester monomer may be treated with the trialkyl phosphite either neat or dissolved in an organic solvent. Effective organic solvents include, for example, an aromatic solvent such as benzene, toluene, xylenes, and ethyl benzene; hydrocarbon solvent such as n-hexane, n-heptane, and cyclohexane; and ketones which will not react rapidly with phosphite esters, such as methyl isobutyl ketone. Preferred solvents include benzene, toluene, and xylene because of their low cost and efficacy. Treatment of the acid or ester monomer without solvent usually is effective and is preferred. Treatment of the acid or ester monomer can be carried out batchwise, that is, by adding the phosphite or phosphite solution to the acid or ester in one or more addition step, mixing with stirring or shaking during the hold time, and then distilling the treated monomer, if desired, in a batch mode. Alternatively the process treatment may be carried out in a continuous manner, that is, by introducing the acid or ester monomer and the phosphite or phosphite solution into a mixer, such as in a continuously stirred tank reactor (CSTR) or in a feed line, continuously mixing the components during the holding time, and then feeding the treated monomer mixture into a hold tank, or into a distillation column and distilling continuously, if desired. Distilling the so-treated monomer mixture is a preferred method in obtaining a further purified monomer.

EXAMPLES

General

Materials: Butyl acrylate (BA) was used as a test monomer and was obtained by acid-catalyzed esterification of acrylic acid (AA) with butyl alcohol. The acrylic acid, also used as a test monomer, was prepared from propylene by conventional oxidation methods. Methyl methacrylate (MMA) also was used as a test monomer and was obtained by conventional acetone cyanohydrin processing and distillation. Analysis of a typical MMA sample showed the presence of 1 to 3 parts per million (ppm) of 2,3-butanedione. Stock solutions with higher 2,3-butanedione (2,3-BD) levels were prepared using 2,3-BD commercially available (Aldrich Chemical Co.) and were used for treatment evaluation without further purification. Specific stock solution analyses are noted where appropriate. Trimethyl phosphite (TMP) and triphenyl phosphite (TPP) were obtained commercially (Aldrich Chem. Co.) and used without further purification.

Analyses: Analysis of carbonyl impurity level was carried out by gas-liquid chromatography (glc) under calibrated conditions. Carbonyl impurity level as low as several parts per million (ppm) in the monomer was detectable with an estimated precision, at levels under 100 ppm, of ±1 ppm. At 2,3-BD levels higher than 1000 ppm, analyses were conducted by conventional Ultraviolet/Visible ("UV/Vis") spectrophotometry. Color was measureable by visual comparison and also by a standard method (the "Platinum-Cobalt Color Test Method ASTM D 1209"). Generally, it was observed that color reduction correlated with the reduction of carbonyl impurity level as measured by glc or spectrophotometric methods.

Abbreviations not previously defined include p-benzoquinone (p-BQ); gram (g); millimeter (mm); centi-

Example 1

Purification of Butyl Acrylate with TMP

A stock butyl acrylate (BA) sample (100 g) was treated with p-BQ (0.02 g) to provide a BA stock solution. Gas liquid chromatographic ("glc") analysis of the BA stock solution showed that it contained 233 ppm of p-benzoquinone; it was a lemon yellow color. Trimethyl phosphite (TMP), 1.15 g, 0.00927 moles, 50 molar ratio to p-BQ, was added and the resulting treated monomer mixture stirred at 22° C. for 17 hrs. Analysis of the so-treated mixture showed that it contained 60 ppm p-BQ, a 74.2% reduction of the quinone, and the yellow color was ably diminished.

Examples 2–5

Additional Tests with BA Stock Solution of Example 1

Examples 2–5 were treated similarly to the sample treatment described in Example 1. The treatments and results of these so-treated Examples are summarized in Table 1 and are relative to the p-BQ treated stock solution originally containing 233 ppm of p-BQ. Under the ambient temperature test conditions described, it was found that a molar ratio even as low as 1:1 reduced the p-BQ level by nearly 20%; a ratio of 5:1 reduced p-BQ by almost one third and noticeably reduced the yellow color in the treated sample.

TABLE 1 p-BQ Level in BA Before and After Treatment with TMP

| Example No. | TMP grams | Molar Ratio[1] | p-BQ (ppm) After Treatment | % Reduced [2] |
|---|---|---|---|---|
| 2 | 0.46 | 20 | 77 | 67.0 |
| 3 | 0.23 | 10 | 99 | 57.5 |
| 4 | 0.11 | 5 | 158 | 32.2 |
| 5 | 0.02 | 1 | 187 | 19.7 |

[1]Moles of phosphite to moles of p-BQ.
[2]Relative to the BA stock solution originally containing 233 ppm p-BQ.

Example 6

Purification of Acrylic Acid with TMP p-Benzoquinone (0.02 g) was added to a stock sample of acrylic acid (AA; 100 g) to yield an AA stock solution. Analysis of the AA stock solution showed that it contained 178 ppm of p-BQ. TMP (1.15 g, 0.00927 moles, a 50 molar ratio to p-BQ) was added and the resulting treated monomer mixture stirred at 22° C. for 17 hrs. Analysis of the mixture showed that it contained <1 ppm of p-benzoquinone. This result demonstrated the effectiveness of TMP in reducing (by >99%) the p-BQ level in AA at a TMP to impurity molar ratio of 50 to 1.

Examples 7–10

Additional Tests with AA Stock Solution of Example 6

Examples 7–10 were treated in the same way as described in Example 6. The treatments and results of these Examples are summarized in Table 2 and are relative to the p-BQ treated stock solution originally containing 178 ppm of p-BQ. All ratios tested here showed reduction in the p-BQ level; at a ratio as low as 5:1, TMP reduced p-BQ level by one-third under the thermally mild test conditions used. Even a 1:1 ratio reduced p-BQ level by more than a substantial level of 10%, specifically, by 18%.

TABLE 2 p-BQ Level in AA Before and After Treatment with TMP

| Example No. | TMP grams | Molar Ratio[1] | p-BQ (ppm) After Treatment | % Reduced [2] |
|---|---|---|---|---|
| 6 | 1.15 | 50 | <1 | >99 |
| 7 | 0.46 | 20 | 29 | 85 |
| 8 | 0.23 | 10 | 88 | 55 |
| 9 | 0.11 | 5 | 132 | 33 |
| 10 | 0.02 | 1 | 161 | 18 |

[1]Moles of phosphite based on moles of p-BQ.
[2]Relative to the analysis of the AA stock solution originally containing 178 ppm of p-BQ.

Example 11

Purification of Butyl Acrylate with Triphenyl Phosphite

Example 11 was prepared and treated in the same way as described in Example 1 except that triphenyl phosphite (TPP) was used instead of trimethyl phosphite. Thus, TPP was added (0.57 grams, 10 molar ratio to p-BQ) to 100 grams of a fresh BA stock solution prepared with 200 ppm of p-BQ (glc analysis showed 209 ppm). The treated monomer mixture was stirred at 23° C. for an 18 hour holding time. The level of p-BQ after the holding time was 92 ppm, a reduction of more than 50%.

Examples 12–15

Purification of MMA with TMP

A sample (100 grams) of stock MMA was inhibited with 200 ppm of the mono methyl ether of hydroquinone (MeHQ). To this monomer solution was added an amount of 2,3-butanedione (2,3-BD) to provide the following test solutions identified as Example No./2,3-BD concentration in ppm: 12/5.4; 13/21.6; 14/99.6. Each so-prepared monomer test solution was added to a reaction vessel equipped with a magnetic stir bar and stirrer. GLC analyses of the respective test solutions showed the 2,3-BD concentrations summarized in Table 3.

A ten molar ratio of TMP relative to the known 2,3-BD concentration was added to each vessel. The reaction vessels containing the treated test example solutions were heated to 60° C. in a water bath and kept at this temperature for three hours with stirring. One and three hour samples were collected for each Example for GLC analysis. Care was taken to exclude light from the reaction vessels during the reaction. The resulting concentration data are summarized in Table 3. The results of these tests using a mole ratio of 10:1 show that 2,3-BD levels are measurably reduced under these conditions; 2,3-BD concentrations of about 100 ppm are reduced by 50% after 1 hr and by 63% after 3 hrs, at 60° C., and the color was visibly improved.

TABLE 3

2,3-BD Level in MMA Before and After Treatment with TMP

| Example No. | TMP grams | Mole Ratio[1] | 2,3-BD (ppm) Before Treatment | After 1 hr Treatment | After 3 hr Treatment | % Reduced[5] |
|---|---|---|---|---|---|---|
| Monomer solution | 0 | 0 | 1.2[2] | — | — | 0 |
| 12 | 0.0072 | 10 | 5.4[3] | 5 | 5.0[4] | 8 |
| 13 | 0.0288 | 10 | 22 | 19 | 15 | 31 |
| 14 | 0.144 | 10 | 100 | 50 | 37 | 63 |

[1]Moles of added phosphite to moles of 2,3-butanedione.
[2]Average of three analyses: 1.0, 1.3 & 1.4 ppm.
[3]Average of two analyses: 5.6 & 5.1 ppm.
[4]Average of two analyses: 5.0 & 4.9 ppm.
[5]Based on difference between known 2,3-BD level before treatment and after 3 hrs.

Examples 15–30

Additional Examples of the Purification of MMA with TMP

A sample (20 grams) of a stock solution of MMA inhibited with 10 ppm of MeHQ also contained the indicated added amount of 2,3-butanedione (the Examples identified as follows: Example No./2,3-BD concentration in wt %: Ex. Numbers 15–18/2.0; 19–22/1.0; 23–26/0.5; 27–30/0.25). Each sample was added to a reaction vessel equipped with a magnetic stir bar and stirrer. UV/Vis analyses of the described monomer stock solutions used for the following Example testing showed the following initial 2,3-BD molar concentrations at 26° C.: Exs. 15–18/0.22188; Exs. 19–22/0.10965; Exs. 23–26/0.05494; Exs. 27–30/0.02749. This operation was carried out four times for each of the described four Example groups of stock solutions for a total of sixteen reaction vessels. TMP was added to each vessel in varying molar excesses as summarized in Table 4. Care was taken to exclude light from the reaction vessels during the reaction. The vessel contents were stirred at ambient temperature and the disappearance of the 2,3-BD was monitored by UV/Vis spectrophotometry under calibrated conditions. The resulting concentration data are summarized in Table 4.

TABLE 4

Molar Concentration of 2,3-Butanedione in MMA After Treatment with TMP at 26° C.

| Example No. | Initial 2,3-BD Concentration in Stock Solution (M)[1] | Added TMP grams | Added TMP Mole Ratio[2] | Molar Concentration of 2,3-BD(M)[3] Treatment 1 hr | Molar Concentration of 2,3-BD(M)[3] Treatment 2 ¼ Hr | % Reduced[4] |
|---|---|---|---|---|---|---|
| 15 | 0.22188 | 0.576 | 1 | 0.106736 | 0.073629 | 58 |
| 16 | " | 1.153 | 2 | 0.041248 | 0.016402 | 91 |
| 17 | " | 1.730 | 3 | 0.011285 | 0.001883 | 99 |
| 18 | " | 2.306 | 4 | 0.002797 | 0.000059 | 100 |
| 19 | 0.109821 | 0.288 | 1 | 0.079821 | 0.063912 | 42 |
| 20 | " | 0.576 | 2 | 0.054059 | 0.033066 | 70 |
| 21 | " | 0.865 | 3 | 0.034683 | 0.015010 | 86 |
| 22 | " | 1.153 | 4 | 0.022697 | 0.007356 | 93 |
| 23 | 0.054635 | 0.144 | 1 | 0.045978 | 0.038442 | 30 |
| 24 | " | 0.288 | 2 | 0.038379 | 0.027283 | 50 |
| 25 | " | 0.432 | 3 | 0.031861 | 0.019190 | 65 |
| 26 | " | 0.576 | 4 | 0.025353 | 0.012520 | 77 |
| 27 | 0.027736 | 0.072 | 1 | 0.024914 | 0.023376 | 15 |
| 28 | " | 0.144 | 2 | 0.022603 | 0.020009 | 27 |
| 29 | " | 0.216 | 3 | 0.020113 | 0.016547 | 40 |
| 30 | " | 0.288 | 4 | 0.018001 | 0.013956 | 49 |

[1]Calculated molar concentrations based on added reagent weights. The Absorbance vs molar concentration plot is non-linear at the 2,3-BD concentration used in Examples 15–18. Molar concentrations calculated based on weights versus those calculated from the solution calibration plot (weight/calibration plot in M: 0.22188/0.175371; 0.109821/0.109648; 0.054635/0.054936; 0.027736/0.027490). (Table 4 Notes, continued)
[2]Moles of added phosphite relative to moles of 2,3-butanedione.
[3]Determined by UV/Vis Spectrophotometry. Calibration plots of standard solutions of 2,3-BD in methyl methacrylate followed Beer's law in the molar concentration range between 0.0068 to 0.1098M and exhibited a correlation factor (R) of 0.99998.
[4]Based on the difference between the 2,3-butanedione level before treatment (Calculated wt % 2,3-BD/Observed M by UV/Vis: 2.0/0.17537; 1.0/0.10965; 0.5/0.05494; 0.25/0.02749) and after a reaction time of two hours and 15 minutes.

Examples 31–38

Treatment of MMA Containing 2,3-BD

A sample (20 grams) of stock solution of MMA inhibited with 200 ppm of MeHQ containing 0.25 wt % of 2,3-butanedione was added to a reaction vessel equipped with a magnetic stir bar and stirrer. UV/Vis analysis of the stock solution showed a 2,3-BD molar concentration of 0.027547M in MMA at 26° C. This operation was repeated seven times for a total of eight reaction vessels charged with the same stock solution. TMP was added to each vessel in varying molar excesses as summarized in Table 5. Care was taken to exclude light from the reaction vessels during the reaction. Four vessels were heated to 60° C. in a water bath. The remaining four vessels were allowed to react at 26° C. The reduction of 2,3 BD was monitored by UV/Vis spectrophotometry for these eight Examples under calibrated conditions. The resulting concentration data are summarized in Table 5.

TABLE 5

Molar Concentration of 2,3-BD in MMA After Treatment with TMP at 26° and 60° C.

| Example No. | Reaction Temp. (°C.) | Added TMP grams | Added TMP eq[1] | Molar Concentration[2] of 2,3-BD(M) Treatment 1 hr | Molar Concentration[2] of 2,3-BD(M) Treatment 2 hrs 15 mins | % Reduced[3] |
|---|---|---|---|---|---|---|
| 31 | 26 | 0.072 | 1 | 0.025186 | 0.023299 | 15 |
| 32 | 26 | 0.144 | 2 | 0.023116 | 0.019748 | 28 |
| 33 | 26 | 0.216 | 3 | 0.021442 | 0.017022 | 38 |
| 34 | 26 | 0.288 | 4 | 0.019264 | 0.014197 | 48 |
| 35 | 60 | 0.072 | 1 | 0.016919 | 0.011826 | 57 |
| 36 | 60 | 0.144 | 2 | 0.009785 | 0.003949 | 86 |
| 37 | 60 | 0.216 | 3 | 0.005698 | 0.001048 | 96 |
| 38 | 60 | 0.288 | 4 | 0.003037 | 0.000015 | 99 |

[1]Moles of added phosphite relative to moles of 2,3-butanedione.
[2]Determined by UV/Vis Spectrophotometry. Calibration plots of standard solutions of 2,3-butanedione in methyl methacrylate followed Beer's law in the molar concentration range between 0.0068 to 0.1098M and exhibited a correlation factor (R) of 0.99998.
[3]Based on difference between the 2,3-butanedione level before treatment (M = 0.027547) and after a reaction time of two hours and 15 minutes.

The data of Table 5 show that a molar ratio of TMP to 2,3-BD of 4 to 1 reduces 2,3-BD level in MMA by nearly one-half at 26° C. after 2 hrs. and 15 min. At 60° C., exposure of a similar sample to the same ratio and time reduced 2,3-BD level to 1% of its original level.

Example 39

Treatment and Batch Distillation Under Reduced Pressure of MMA Containing 2,3-BD A stock solution sample (2000 g) of 2,3-BD in MMA, MeHQ (15 ppm) and a nitroxyl radical trap (1000 ppm) was added to a 4-neck, 3 liter round-bottom flask equipped with 1) a Hempel distilling column (25 mm diameter by 40 cm length) packed with 6 mm protruded metal packing, 2) heating mantle, 3) thermocouple, 4) temperature controller, 5) distillation head, 6) a septum inlet adapter fitted with a rubber septum for bottoms sampling, 7) vacuum system, 8) magnetic stir bar and 9) stirrer. GLC analysis of the stock solution showed a 2,3-BD concentration of 227 ppm. Trimethyl phosphite (2.88 g, equivalent to a 4:1 molar ratio relative to 2,3-BD) was added to the stock solution. The reaction mixture was heated to 60° C. and stirred for 7.5 hrs at atmospheric pressure. Samples (2 g each) of the reaction mixture were collected at one hour intervals and analyzed by GLC. The results of these analyses are summarized in Table 6 for Samples 39 A–H. A second portion of trimethyl phosphite (0.72 g, equivalent to a 1:1 molar ratio relative to the starting level of 2,3-BD) was added to the stock solution after hour five. After 7.5 hrs, heat input was discontinued and the reaction mixture was allowed to stir for seventeen hours at ambient temperature and pressure.

TABLE 6

Concentration of 2,3-BD in MMA After Treatment with TMP at 60° C.

| Sample | Added TMP grams | Added TMP eq[1] | Time Index (hr) | ppm | % Reduced[2] |
|---|---|---|---|---|---|
| A | 2.88 | 4 | 0 | 227 | 0 |
| B | — | — | 1 | 184 | 18 |
| C | — | — | 2 | 156 | 31 |
| D | — | — | 3 | 140 | 38 |
| E | — | — | 4 | 128 | 44 |
| F | — | — | 5 | 115 | 49 |
| G | 0.72 | 1 | 6 | 96 | 58 |
| H | — | — | 7 | 84 | 63 |

[1]Moles of added trimethyl phosphite relative to moles of 2,3-butanedione.
[2]Based on the difference between the 2,3-BD level before treatment (227 ppm) and after the reported time index.

The treated batch was heated for an additional 1.5 hrs at 60° C. and sampled (Table 7, sample I) prior to distillation. The system pressure was reduced until MMA began to distill at approximately 182 mm Hg. Samples of both overhead and bottom streams were collected every hour and analyzed by GLC throughout the distillation to determine the 2,3-BD concentration. Results are summarized in Table 7 (Samples J–O).

TABLE 7

Concentration of 2,3-BD in Distilled MMA After Treatment with TMP at 60° C.

| Ex. 39 Sample | Time Index (hr) | Mass of Fraction (g) | ppm overhead | ppm bottoms |
|---|---|---|---|---|
| I | 0 | 0 | — | 49 |
| J | 1 | 160 | 57 | 48 |
| K | 2 | 236 | 33 | 39 |
| L | 3 | 197 | 27 | 35 |
| M | 4 | 204 | 22 | 37 |
| N | 5 | 193 | 18 | — |
| O | 6[1] | 96 | 16 | 41 |

[1]Distillation concluded on the half hour.

The distilled (overhead) samples had a very pale yellow color (estimated at less than 100 on the Pt-Co color scale) which color decreased in approximate proportion to the measured decrease in the 2,3-BD concentration.

Comparative Example 1

MMA Treatment Without TMP

Comparative Example 1 was prepared and treated in the same way as described in Example 39 except that the trimethyl phosphite treatment was omitted. Distillation of the 2,3-BD doped sample of MMA was begun as soon as the bottoms temperature equilibrated to 60° C. and yielded Comparative Samples A–G, Table 8.

TABLE 8

Concentration of 2,3-BD in Untreated Distilled MMA at 60° C.

| Sample | Time Index (hr) | Mass of Fraction (g) | ppm overhead | ppm bottoms |
|---|---|---|---|---|
| A | 0 | 0 | — | 240 |
| B | 1 | 195.2 | 597 | 230 |
| C | 2 | 144.6 | 502 | 192 |
| D | 3 | 186.2 | 402 | 158 |
| E | 4 | 189.4 | 239 | 147 |
| F | 5 | 193.0 | 299 | 113 |
| G | 6[1] | 95.5 | 209 | 110 |

[1]Distillation concluded on the half hour.

All of the collected fractions had a strong lemon-yellow coloration and were estimated to be greater than 150 Pt-Co color. Comparison of Tables 7 & 8 shows the dramatic difference in the concentration of 2,3-BD between treated and untreated batch-distilled MMA.

Example 40

Treatment of MAA Containing 2,3-BD

A stock solution sample (200 g) of 2,3-BD in MAA, MeHQ (250 ppm) and a nitroxyl radical trap (1000 ppm) was added to a 3-neck, 500 mL round-bottom flask equipped with 1) heating mantle, 2) thermocouple, 3) temperature controller, 4) reflux condenser, 5) magnetic stir bar and 6) stirrer. GLC analysis of the stock solution showed a 2,3-BD concentration of 227 ppm. Trimethyl phosphite (0.37 g, equivalent to a 5:1 molar ratio relative to 2,3-BD) was added to the stock solution. The reaction mixture was heated to 60° C. and stirred for 7 hours at atmospheric pressure. Samples (2 g each) of the reaction mixture were collected at one hour intervals and analyzed by GLC. The results of these analyses are summarized in Table 9 for Samples 40 A–H. A second portion of trimethyl phosphite (0.07 g, equivalent to a 1:1 molar ratio relative to the starting level of 2,3-BD) was added to the stock solution after hour four. After the seventh hour, heat input was discontinued and the reaction terminated; results are included in Table 9.

TABLE 9

Concentration of 2,3-BD in MAA After Treatment with TMP at 60° C.

| Sample | Added TMP grams | Added TMP eq[1] | Time Index (hr) | ppm | % Reduced[2] |
|---|---|---|---|---|---|
| A | 0.37 | 5 | 0 | 227 | 0 |
| B | — | — | 1 | 86 | 62 |
| C | — | — | 2 | 86 | 62 |
| D | — | — | 3 | 85 | 63 |
| E | — | — | 4 | 89 | 61 |
| F | 0.07 | 1 | 5 | 65 | 71 |
| G | — | — | 6 | 67 | 70 |
| H | — | — | 7 | 63 | 72 |

[1]Moles of added trimethyl phosphite relative to moles of 2,3-butanedione.
[2]Based on the difference between the 2,3-BD level before treatment (227 ppm) and after the reported time index.

We claim:

1. A process for reducing carbonyl impurity present in an $\alpha,\beta$-unsaturated carboxylic acid or its alkyl ester, comprising:
   a) admixing
      (i) a monomer selected from the group consisting of an $\alpha,\beta$-unsaturated carboxylic acid, an $\alpha,\beta$-unsaturated carboxylic acid alkyl ester, and mixtures thereof, the monomer containing a carbonyl impurity present at an original level of at least 50 parts per million, with
      (ii) a phosphite ester selected from the group consisting of a trialkyl phosphite and a triphenyl phosphite, wherein the molar ratio of phosphite ester to carbonyl impurity in the monomer is 1:1 to 50:1, thereby forming a treated monomer mixture; and
   b) holding the treated monomer mixture at a temperature of from 20° C. to 150° C., thereby reducing the carbonyl impurity in the monomer by at least 10 weight percent of the original level of the carbonyl impurity.

2. The process of claim 1 wherein the phosphite ester is selected from the group consisting of trimethyl phosphite, triethyl phosphite, tributyl phosphite, and triphenyl phosphite.

3. The process of claim 1 wherein the $\alpha,\beta$-unsaturated carboxylic acid is selected from at least one of a $C_3$–$C_{10}$ $\alpha,\beta$-unsaturated carboxylic acid.

4. The process of claim 3 wherein the $\alpha,\beta$-unsaturated carboxylic acid is selected from acrylic acid or methacrylic acid.

5. The process of claim 1 wherein the $\alpha,\beta$-unsaturated carboxylic acid alkyl ester is selected from at least one ester of a $C_3$–$C_{10}$ $\alpha,\beta$-unsaturated carboxylic acid and a $C_1$–$C_{10}$ alcohol.

6. The process of claim 5 wherein the $\alpha,\beta$-unsaturated carboxylic acid ester is selected from acrylic acid alkyl ester or methacrylic acid alkyl ester.

7. The process of claim 6 wherein the α,β-unsaturated carboxylic acid alkyl ester is selected from the group consisting of methyl acrylate, ethyl acrylate, butyl acrylate, methyl methacrylate, and butyl methacrylate.

8. The process of claim 1 further comprising the step of distilling the treated monomer mixture following the holding of step (b).

9. A purified monomer comprising:
 a) a monomer selected from the group consisting of an α,β-unsaturated carboxylic acid, an α,β-unsaturated carboxylic acid alkyl ester, and mixtures thereof, the monomer containing a carbonyl impurity present at an original level of at least 50 parts per million;
 b) a phosphite ester selected from the group consisting of trialkyl phosphite and triphenyl phosphite, wherein the phosphite ester is present in a molar ratio of from 1:1 to 50:1 of the original level of the carbonyl impurity in the monomer.

10. A polymer prepared from the purified monomer of claim 9.

11. An article prepared from the polymer of claim 10 in a form selected from the group consisting of an optical fiber, a light transmission fiber, a flexible light pipe up to 15 millimeters in diameter, a light diffuser, and a light deflector.

* * * * *